(12) United States Patent
Richelsoph

(10) Patent No.: US 7,935,138 B1
(45) Date of Patent: May 3, 2011

(54) ACTIVE BONE SCREW

(76) Inventor: Marc E. Richelsoph, Charlotte, NC (US)

( * ) Notice: Subject to any disclaimer, the term of this patent is extended or adjusted under 35 U.S.C. 154(b) by 0 days.

(21) Appl. No.: 12/844,974

(22) Filed: Jul. 28, 2010

(51) Int. Cl.
*A61B 17/86* (2006.01)
*A61B 17/04* (2006.01)
*A61F 2/08* (2006.01)

(52) U.S. Cl. ........ 606/313; 606/309; 606/314; 606/326; 606/327

(58) Field of Classification Search .................. 606/310, 606/313, 314, 315, 327, 328; 411/16, 17, 411/25, 251, 252, 325, 392, 411, 412, 421, 411/438, 516
See application file for complete search history.

(56) References Cited

U.S. PATENT DOCUMENTS

| 422,307 A * | 2/1890 | Libbey .......................... 411/412 |
| 2,520,232 A | 8/1950 | Berez |
| 2,524,480 A | 10/1950 | Schenk |
| 2,777,718 A | 1/1957 | Vegren |
| 3,515,027 A | 6/1970 | Textrom |
| 3,813,718 A * | 6/1974 | Kamiya .......................... 470/10 |
| 4,040,326 A | 8/1977 | Breed |
| 4,075,925 A | 2/1978 | Lerich |
| 4,764,067 A * | 8/1988 | Kawashima .................. 411/310 |
| 6,224,311 B1 | 5/2001 | Lutkus et al. |
| 6,276,883 B1 | 8/2001 | Unsworth |
| 6,371,709 B1 * | 4/2002 | Papafotiou et al. ........... 411/412 |
| 6,494,657 B2 | 12/2002 | Unsworth |
| 6,860,691 B2 | 3/2005 | Unsworth |
| 7,063,701 B2 | 6/2006 | Michelson |
| 7,165,925 B2 | 1/2007 | Unsworth |
| 7,281,925 B2 * | 10/2007 | Hall .............................. 433/174 |
| 2005/0187555 A1 | 8/2005 | Bierdermann |
| 2008/0004626 A1 | 1/2008 | Glazer |
| 2009/0118831 A1 | 5/2009 | Trieu |
| 2009/0157123 A1 | 6/2009 | Appenzeller et al. |

* cited by examiner

*Primary Examiner* — Thomas C Barrett
*Assistant Examiner* — Andrew Yang
(74) *Attorney, Agent, or Firm* — Kohn & Associates PLLC

(57) ABSTRACT

A bone screw includes a head portion and shank portion. The shank portion includes a regularly outwardly expanding threaded portion.

11 Claims, 6 Drawing Sheets

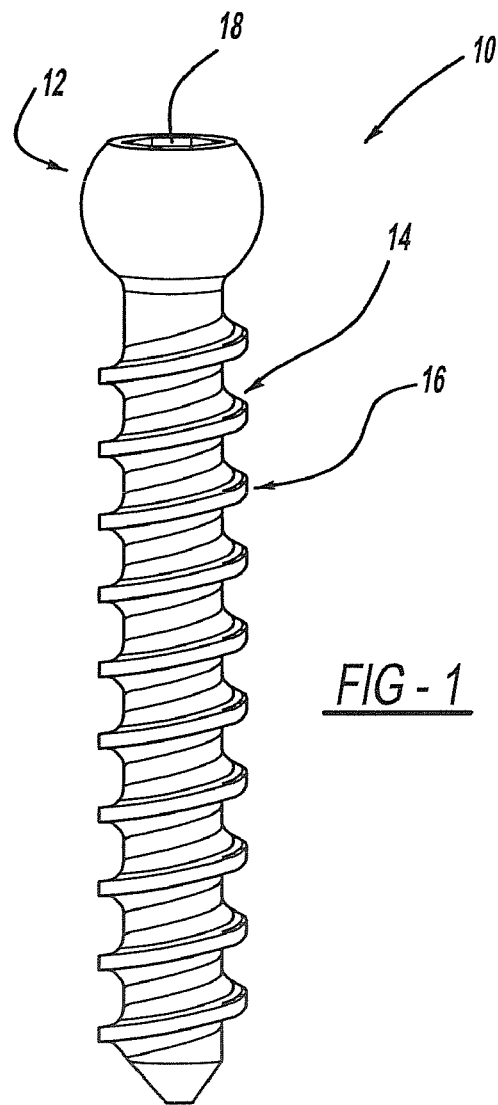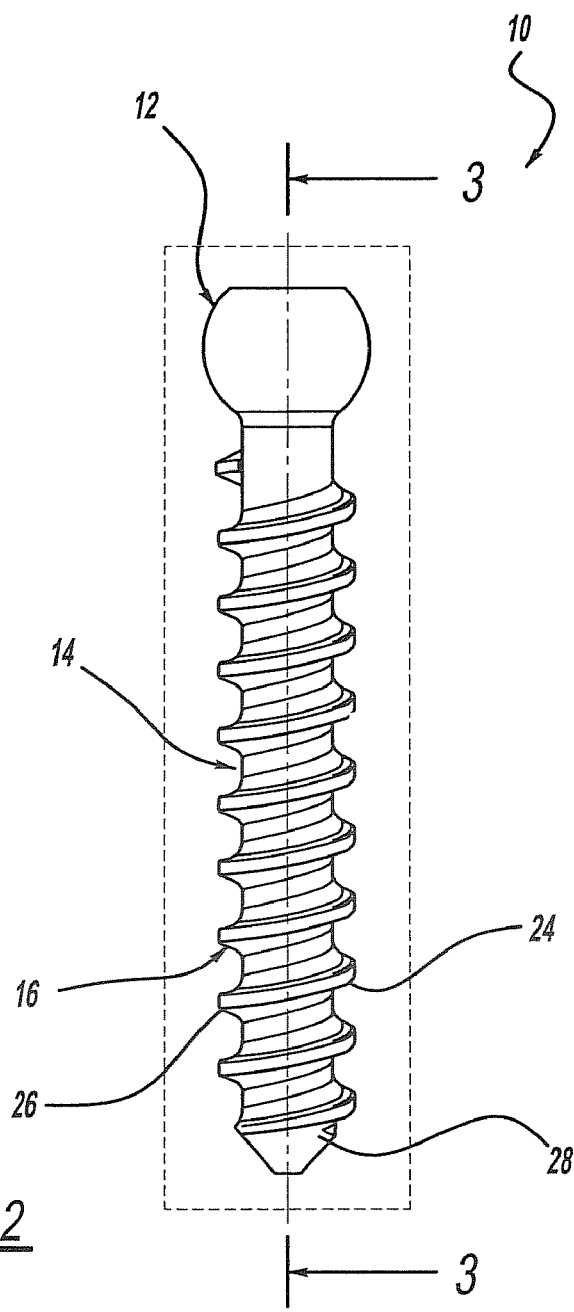
FIG-1
FIG-2

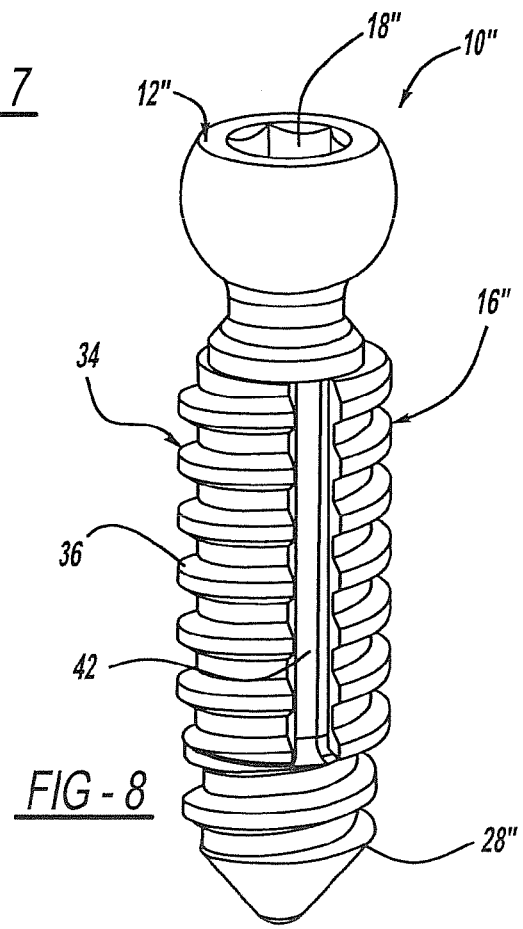
FIG - 8
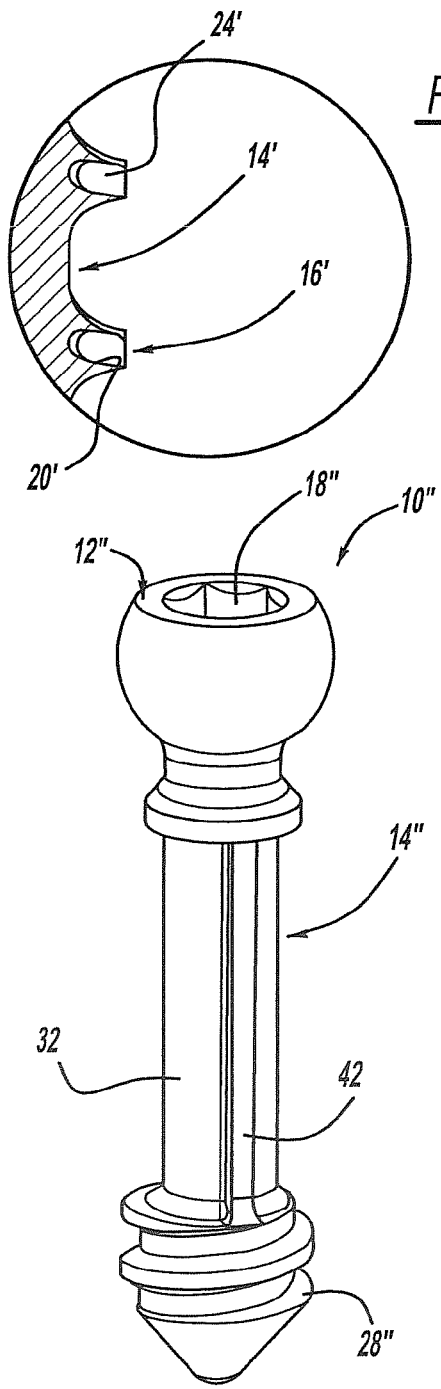
FIG - 7
FIG - 9
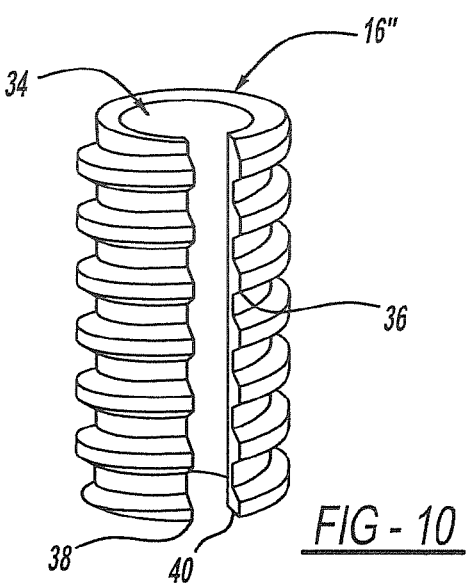
FIG - 10

ACTIVE BONE SCREW

TECHNICAL FIELD

The present invention is directed to the use of screws for orthopedic surgery. More specifically, the present invention relates to bone screws used for repairing fractures and securing orthopedic devices to bone.

BACKGROUND OF THE INVENTION

The use of screws in orthopedic surgery extends back to the latter part of the 1800's, with Riguad implanting Swedish steel screws for repairing a fracture of the olecranon. By 1866, Hansmann of Hamburg, Germany developed the first bone plate and screw device assembly, with the screws being inserted pericutaneously. By the early 1900's, the problem of the screws loosening in the bone socket in which they were inserted was recognized as a significant problem. In response to this problem, new screw designs were developed. Lane designed a screw from wood. However, poor hold in diaphyseal bone led other to use metal for the screw design. Self-tapping screws for orthopedics were developed as well around 1921.

Presently, there are numerous screw designs using different threads and materials. Single and multiple lead threaded screws, with or without self-tapping capabilities, can be found throughout all orthopedics. The most common materials used for these screws are titanium, cobalt chrome, and stainless steel. Bioresorbable screws are also used, made from various compositions well known in the art. Examples of bioresorbable materials commonly used in today's orthopedics include polylactic acid, polyglycolic acid, the L-Isotope form of polylactic acid, and copolymers of polyactic acid and polyglycolic acid.

In spite of recent developments, the basis of the bone screw has remained unchanged, even though loosening of the screw in the socket into which it is seated has become more of an issue with more recent applications of technology. To compensate for these problems, various approaches, such as coatings and better bone inductive or conductive materials have been applied to the surface of the screw. Altering the screw by texturing the screw surface has also been attempted. While these approaches may in some ways address the problem, they are not sufficient to address the current problem of loosening with a number of high-load applications.

A significant part of the correct screw insertion and fixation in any application is the necessity of sufficient "bite" or depth of the actual thread into the bone. In practice, this is accomplished ideally by having an entry hole for the screw matching a minor diameter, such that the entire thread extending from the minor diameter to the major diameter is completely buried in the bone itself. It is apparent that too small a screw will have insufficient thread purchase and be subject to being pulled out of the bone. Too large a screw relative to the entry-hole size creates the risk of overstressing the bone and causing fractures. If sized correctly, a screw will give good holding values, or what is termed pull-out strength, initially. However, what happens under high loads or bone remodeling is a loosening of the screw within its socket.

A number of more recent spinal systems have moved toward the concept of dynamic systems. In these systems, the screw remains the anchor, but the loads are distributed or altered by a device placed between the screws. One such system uses a woven cord to allow flexure in certain directions, but rigidity where needed. Other systems utilize polyetheretherketone (PEEK) polymer rods, flexible rods, or flexible connectors. One aspect that all these have in common is that they change the load on the screw fixation means significantly. Bone screws experience higher loads and flexion/extension of the spine places cyclic loads on the screws which differ than the previous more rigid rod fixation means. This often results in much higher loosening rates in vivo. One current system reports loosening failure rates anywhere from 8%-39%. As expected, the numbers vary with the number of patients, but regardless, 8% failure rate is not an acceptable level, let alone a 39% failure.

The root of the problem discussed above lies in the means of fixation to the bone. Regardless of how the surface of the screw is treated, the technology in screw means of fixation remains almost the same as screws developed in the early 1920's.

Other orthopedic devices face similar drawbacks with regard to bone gripping and remodeling. For example, it is desirable to stabilize cervical interbody fusion systems, such as cages. Such cages often depend on bone healing from one vertebrae, through a cage, to another vertebrae.

In order to address and resolve the problem of loosening, it is a far better approach to allow the screw to adjust to bone remodeling or bone interface damage. Bone interface damage, such as a screw thread being pulled out of the thread in the bone, effectively strips the threads. In a normal screw, loosening then occurs.

SUMMARY OF THE INVENTION

In accordance with the present invention, there is provided a bone screw including a head portion and a shank portion. The shank portion includes a radially outwardly expanding thread.

The present invention further provides a bone screw including a radially outwardly expanding thread.

The present invention further provides a bone screw collar including a flexible body portion having a threaded outer surface and being C-shaped in cross section, the collar having radially compressed and expanded conditions, and two edge surfaces spaced from each other when the collar is in the expanded condition.

The present invention further provides a method of inserting a bone screw into a bone by threading a screw into a bone, and forming a complimentary threaded socket in the bone. A thread of the screw is expanded into the threaded socket as the threaded socket expands with wear over time.

The present invention further provides a method of maintaining a bone screw in a socket formed by the screw in a bone by expanding the thread of the screw into complimentary threads of the socket as the socket wears away over time.

BRIEF DESCRIPTION OF THE DRAWINGS

Other advantages of the present invention or readily appreciated as the same becomes better understood by reference to the following detailed description, when considered in connection with the accompanying drawings, wherein:

FIG. 1 is an elevational side view of a bone screw made in accordance of the present invention;

FIG. 2 is a side view of the inventive bone screw;

FIG. 7 is an enlarged detail of the thread of the screw shown in FIG. 6;

FIG. 8 is an elevational perspective view of a further embodiment of the present invention;

FIG. 9 is an elevational perspective view of the embodiment shown in FIG. 8 without a threaded collar thereon;

FIG. 10 is an elevational perspective view of the collar of the embodiment shown in FIG. 8.

DETAILED DESCRIPTION OF THE INVENTION

Figure 3:
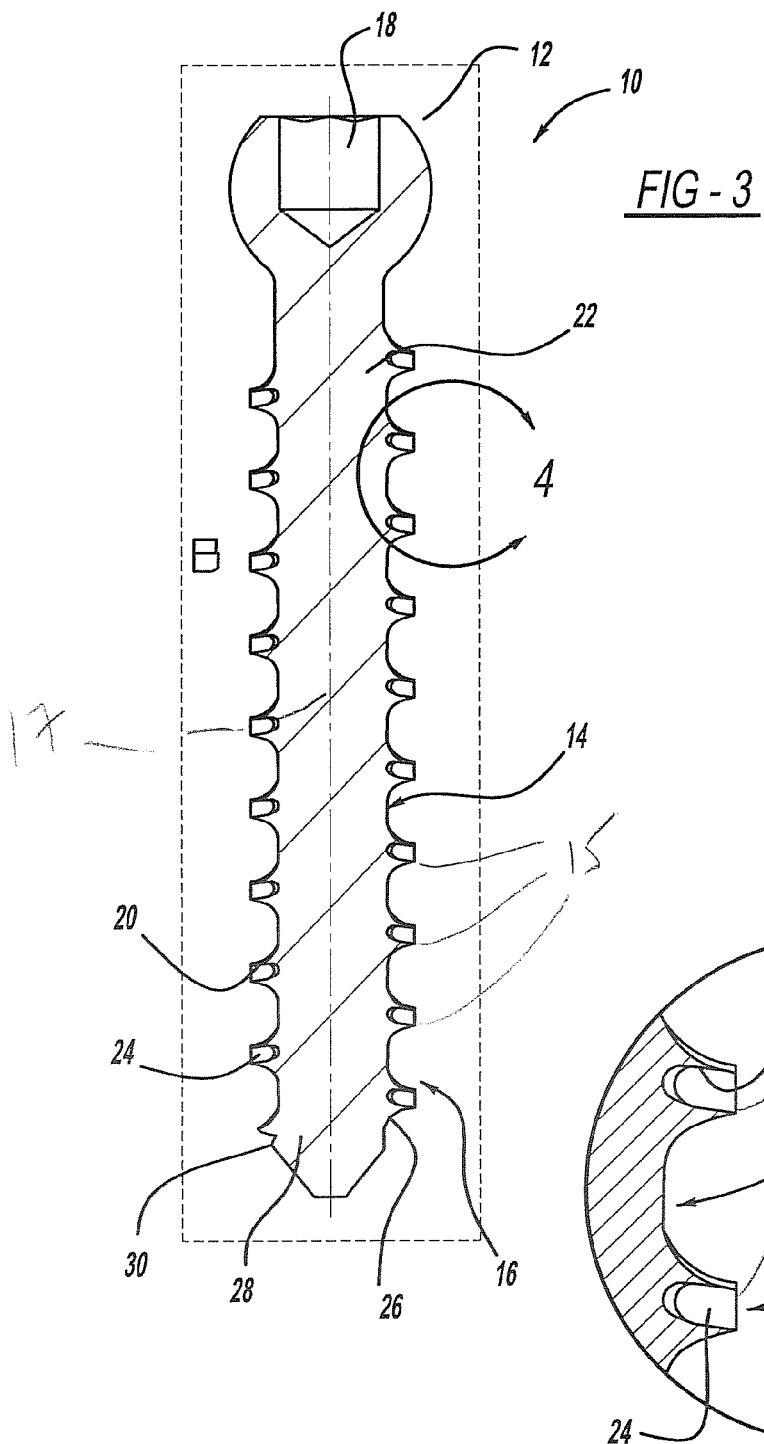
FIG. 3 is a cross sectional view taken substantially along lines A-A of FIG. 2.

A bone screw constructed in accordance with the present invention is generally shown at 10 in the drawings.

Different embodiments of the same structure are indicated by primed numbers in the figures.

Generally, the bone screw 10 includes a head portion, generally shown at 12, and a shank portion generally shown at 14. The shank portion includes a radially outwardly expanding thread generally shown at 16. The radially outwardly expanding thread 16 solves the problems of the prior art by providing an active bone screw which adjusts to bone remodeling or bone interface damage by expanding into the worn area of the bone so as to maintain sufficient bite or depth of the actual thread into the bone. Likewise, where a socket is previously tapped prior to insertion of the screw and the tapped socket has a greater diameter than a normally threaded screw shank, the present invention allows for radially outward expansion of the thread to grip the pre-tapped socket to again provide sufficient bite and/or depth of the actual thread into the bone. Accordingly, the present invention provides an active bone screw, active in the sense that it does not passively remain in a socket as the socket wears and the screw eventually loosens, but rather, the bone screw is active so as to maintain its bite and retention properties in the socket by the thread of the bone screw expanding into the socket as the socket wears.

Another advantage to the present invention is via application of Wolff's Law. The effort here is to place a controlled force on the bone to create a stress condition for favorable remodeling of the bone, to gain better pull out strength and maintain it over time. Accordingly, the present invention provides a novel method of remodeling bone by providing an outwardly radial force from a screw shank 14 while the screw shank 14 is inserted into the bone. Based on this principle, the present invention actually results in an effective reduced wear on the bone as the bone is remodeling in response to the outward pressure placed by the threaded portion 16, during retention of the screw 10, in the bone. Unlike a toggle bolt approach, which is incapable of remodeling or moving with the bone, the present invention effectively creates a bioactive mechanical screw that allows for excellent bone purchase with minimum complexity.

Accordingly, the present invention can take the form of various orthopedic devices, such as screws and other body fusion systems wherein proximate inducement of bone remodeling is desired. In both embodiments set forth, the screw or system includes a body portion including an expandable and compressible portion, preferably a threaded or threaded portion, disposed thereabout. After insertion into a socket or intervertebral space, respectively, the outwardly biasing force of the thread or threaded portion induces the bone remodeling. This results in initial and then continued stabilization of the device or system in situ.

Referring to FIGS. 1-4, the shank portion 14 of the screw 10 provides the main body portion of the screw member, similarly to previously existing portions. The head portion 12 is round and includes a recess 18 therein for receiving an instrument, having the function of a screw driver, to drive the screw 10 into a socket in bone. As alluded to above, the socket may be pre-tapped or the screw 10 may be used to form the socket.

Figure 4:
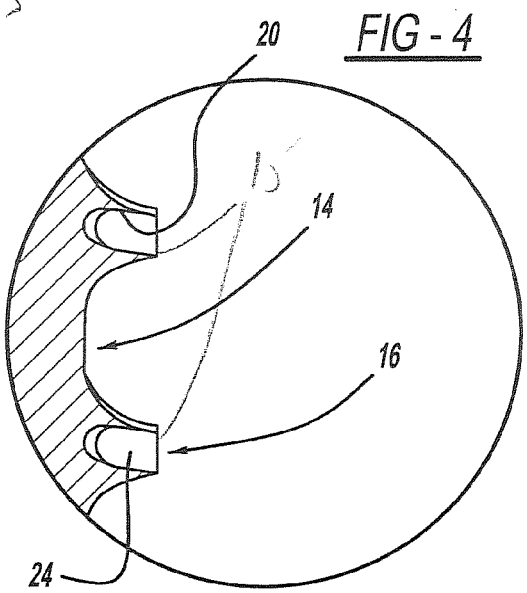
FIG. 4 is an enlarged view of the thread, shown in cross-section, as shown in FIG. 3.
Figure 12:
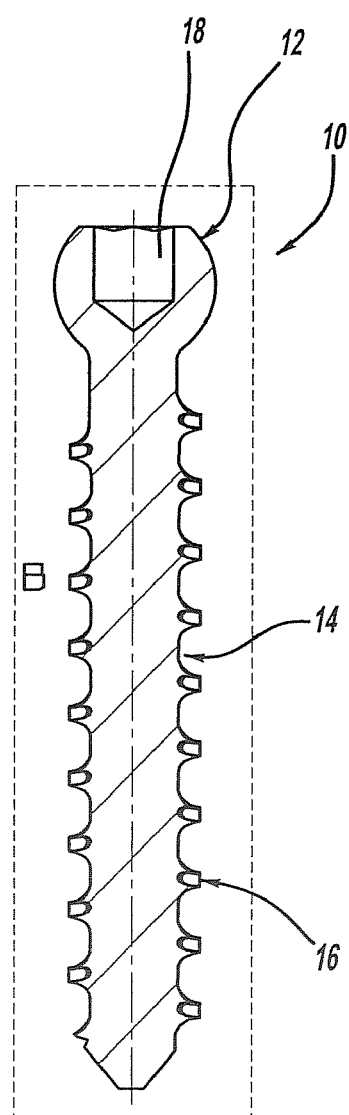
FIG. 12 is an elevational view in cross section of a screw including a thread in a compressed condition.
Figure 13:
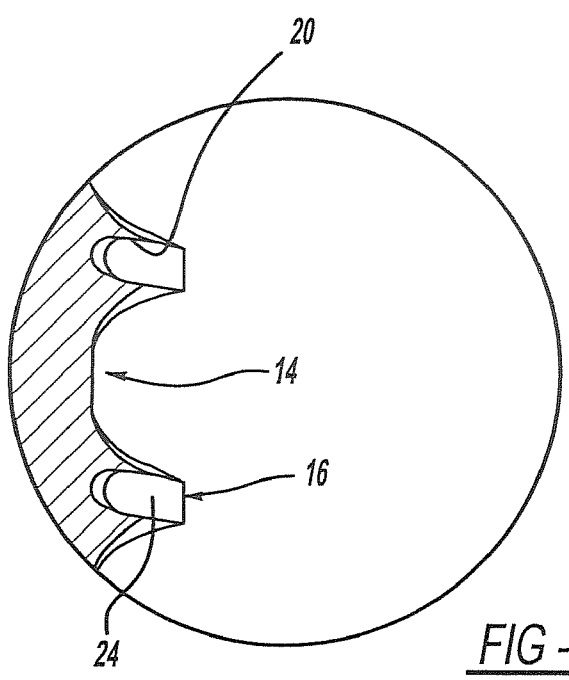
FIG. 13 is an enlarged view of the compressed thread from FIG. 12.
Figure 14:
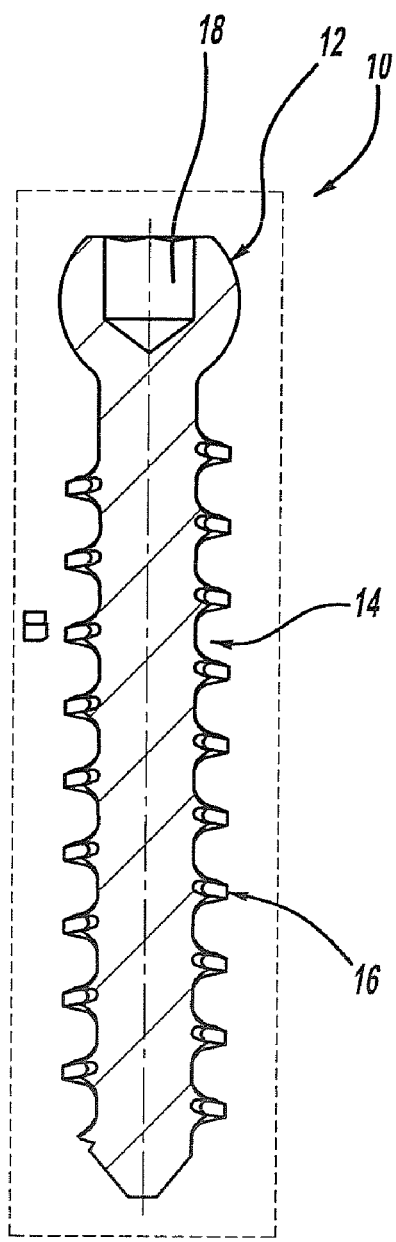
FIG. 14 is an elevational view in cross section of a screw including a thread in an expanded condition.
Figure 15:
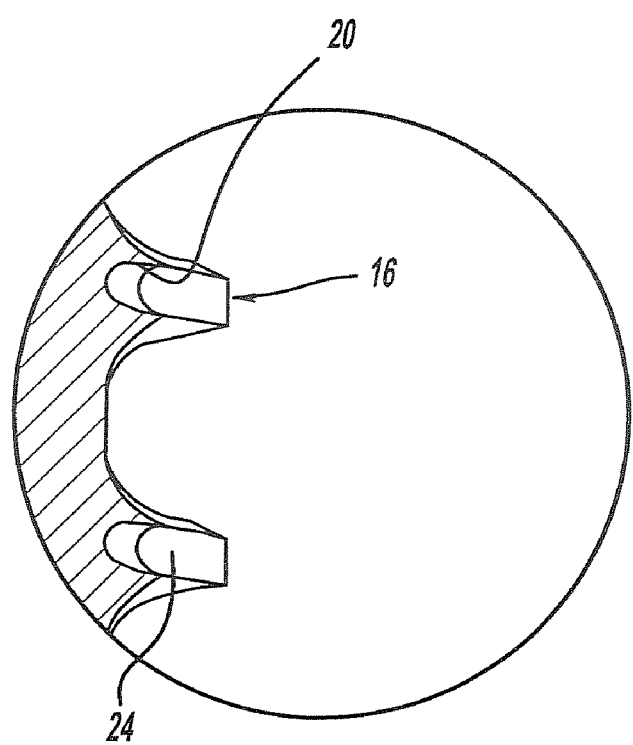
FIG. 15 is an enlarged view of the expanded thread from FIG. 14.

As best shown in FIGS. 3 and 4, the shank portion 14 includes a longitudinally helical thread 16 including an edge 15 including a helical groove 20 along a longitudinal axis 17 of the shank portion 14, the axis being indicated by line 22 in FIG. 3. The thread 16 includes a helical member, shown in the form of a helical spring-type member 24 disposed within the groove 22. The helical spring member 24 is flexible in that in response to radially inward pressure thereon, relative to the axis 22, the spring member 24 will be forced further into and seated further into the groove 20 along the axial length of the shank portion 22, as best shown in FIGS. 12 and 13. Upon release of the axially inward pressure on the helical spring member 24, the helical spring member 24 will bias radially outwardly from the axis 22, as best shown in FIGS. 14 and 15. Thus, the spring member 24 has a compressed condition, as shown in FIGS. 12 and 13, wherein the shank portion 14 is seated within a socket which compresses the spring member 24 radially into the groove 20 and an expanded condition, as shown in FIGS. 14 and 15, wherein the spring member 24 expands radially outwardly into the socket. The grooves of the socket which are complementary to the spring member 24 wear over time. The spring member provides an active element to the screw which is capable of being in a compressed condition upon the screw entering a newly formed socket or forming a newly formed socket while also being able to maintain bite and grip of the socket as the socket wears during use.

At least a lead end 26 of the spring member 24 is securely affixed to and within the groove 20. The remainder of the spring member 24 is solely seated in the groove 20 allowing for not only radially inward and outward movement between said compressed and expanded conditions, but also allowing for linear creep around the length of the shank portion 14. This is necessitated because as the spring member 24 is forced into the compressed condition, such as when the shank portion 14 is first inserted into a newly formed shaft in a bone, or if the screw member is exposed within a compressing instrument to place the shank portion 14 into a socket in a bone, the compression of the spring member 24 will necessarily cause an extension of the length of the spring member 24 in the groove 20. Accordingly, the groove 20 must have a linear length sufficient to continue to capture the extending length of the spring member 24 as it enters into its compressed condition. Thus, the groove 20 includes a linear length greater than a length of the spring member 24 when the spring member 24 is in the expanded condition, allowing for the aforemention linear growth of the spring member 24, as the spring member 24 is compressed into the compressed condition.

While the spring member 24 can be any cross sectional shape, including round and rectangular, in the preferred embodiment the spring member 24 can have an elongated rectangular or oval shape. The advantage is that as the threads 16 expand outwardly, the elongated rectangle or oval shape remains supported by the walls of the groove cut into the socket of the bone into which the screw 10 is disposed. This is a significant aspect of the invention, in that two portions of the screw 10 must work in concert to act as if it was a single component screw to maintain maximum pull out strength.

The shank portion 12 includes a driving element 28 at a distal end thereof from the head portion 12. The driving portion 28 creates the initial contact with the bone. The driving element 28 has a major diameter, shown at 30 in FIG. 3, which is greater than that which would be normally used, as the spring member 24 is in the expanded condition, that being at full diameter. During insertion of the shank portion 14 into a socket of a bone, while forming a socket in a bone as the screw 10 is threaded into the bone, the spring member 24 winds into the groove 20, reducing that diameter of the initially desired pull diameter. For example, for a screw starting off with the spring thread portion 16 at 6.5 mm, as it is threaded into the bone, the spring member 24 winds into the groove 20 to fit a 5.5 mm threaded hole. This allows 1 mm of adjustment by the thread to bone resorbtion, or bone damage and wear. The amount of expansion outward of the thread 16 can be readily adjusted by the design, as well as the actual force applied thereby. While it is advantageous to exert radially outward force, the amount of force must not be too great in order to avoid any risk of fracturing the bone during insertion.

The outward force can range from extremely small loads to very high loads, depending on the diameter of dimension of the thread, material, or material treatment, such as heat treating or cold working. Loads may also vary from application to application. For a pedicle, desired loads would be lower than what would be used to induce remodeling about an interbody spacer that is under higher compressive loads and less concerned about radial loads to the bone socket.

Figures 5, 6:
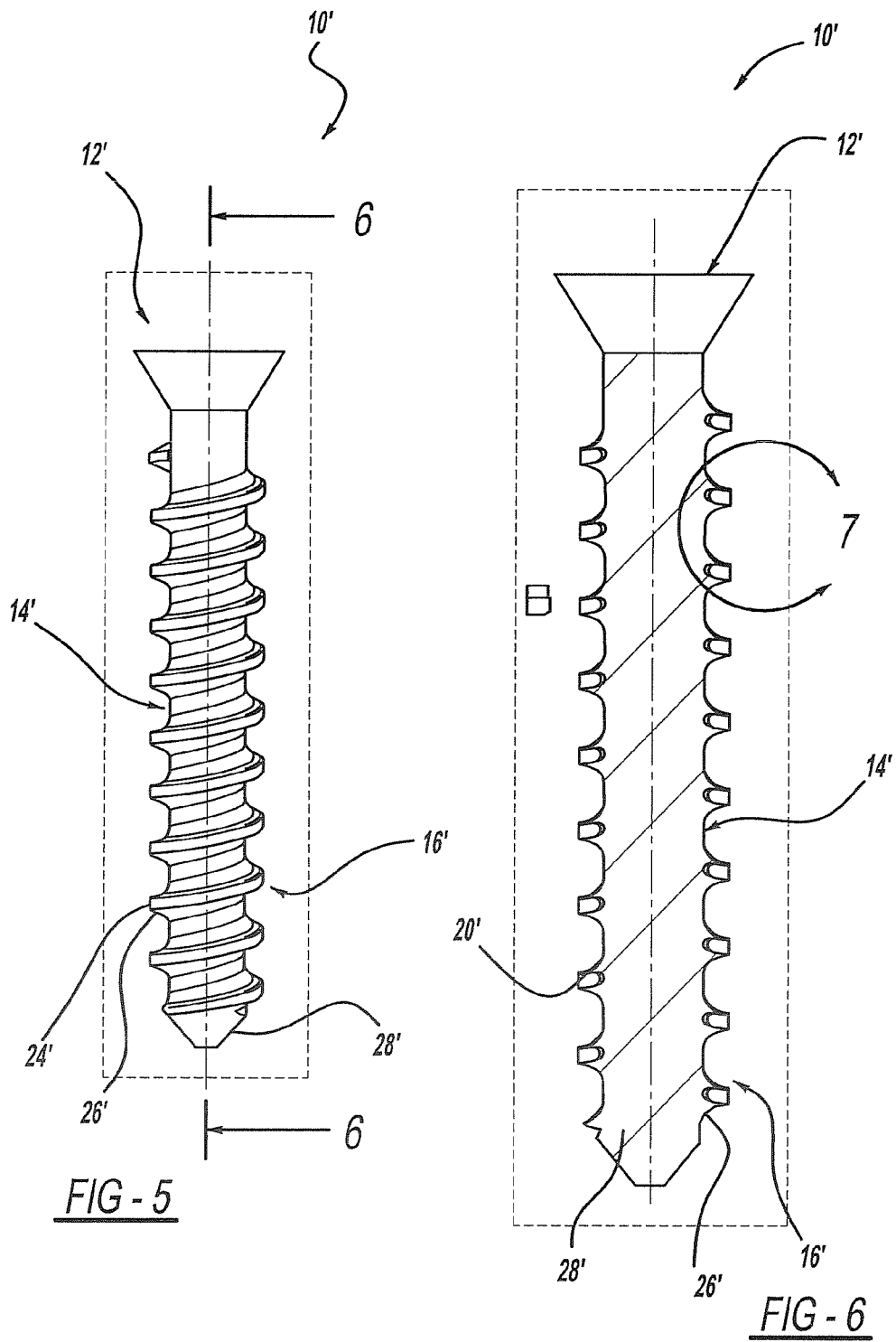
FIG. 5 is an elevational view of the present invention having a self-tapping head.
FIG. 6 is a cross sectional view taken substantially along lines A-A of FIG. 5.

FIGS. 5-7 show a second embodiment of the invention wherein the bone screw 10' is self tapping. That is the head portion 12' is a self tapping head, having a frusto-conical shape as shown in cross section in FIG. 6. However, as noted above, the invention can be used without the self tapping head 12', as shown in the remaining figures. In the case where the self tapping head 12' is utilized, the hole one socket would not need be tapped prior to the insertion of the screw member 10'. In the case where the head 12' is not self tapping, as shown in FIGS. 1-4 and 8-11, the hole would be tapped by a separate instrument and then the screw 10, 10", would be inserted into the tapped hole.

A further embodiment of the present invention is shown in FIGS. 8-11. In this embodiment, and specifically referring initially to FIGS. 8 and 9, the screw member 10" includes a shank portion 14" having a body portion 32 of reduced radial diameter between the head portion 12" and the driving element 28". The shank portion 14" further includes a radially compressible collar generally shown at 34 having an outer threaded surface 36 maintained between the head portion 12" and the driving element 28". The collar 34 has a radially compressed condition wherein a socket wherein the shank portion 14" is seated compresses the collar 34 radially towards the body portion 32 and an expanded condition wherein the collar 34 expands radially outwardly into the socket formed in the bone as the socket wears and expands over time. In other words, the collar 34 performs a similar function to the radially expanding helical spring member 24 so as to be initially in a compressed condition upon entering a socket of a bone and then expanding into the socket to produce bite against the grooved bone surface. As the bone surface of the socket wears or otherwise remodels, the collar 34 is biased radially outwardly so as to maintain bite into the worn or wearing surface.

Figure 11:
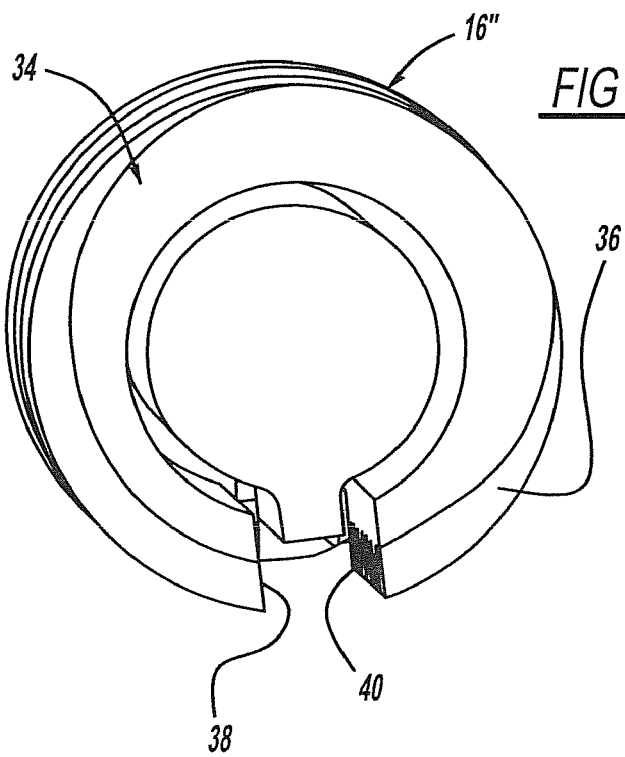
FIG. 11 is a top view of the collar shown in FIG. 10.

More specifically, the collar 34 is substantially C-shaped in cross section and includes spaced opposing edge portions 38, 40, as best shown in FIG. 11. The edged portions 38, 40, are spaced when the collar 34 is in the expanded condition and in close proximity as the collar is compressed into the compressed condition.

In order to create sufficient threading capability of the screw member 10", the collar 34 and threaded surface 36 thereof, cannot rotate around the longitudinal axis of the screw member 10", relative to the screw member 10". Accordingly, the present invention includes a mechanism for preventing relative rotation between the body portion 32 of the shank 14" and the collar 34. Specifically, the body portion 32 includes a radially outwardly projecting portion 42, as best shown in FIG. 9, disposed between the opposing edge portions 38, 40 of the collar 34, defining the mechanism for preventing relative rotation between the collar 34 and the body portion 32. That is, the projection 42 has a lock and key relationship with the collar 34 as it is disposed between the edges 38, 40 of the collar 34. The projection 34 can take on various shapes as long as it provides an abutment against the opposing edges 38, 40, while still being spaced therefrom allowing for expansion and compression of the collar 34.

The threaded collar 34 acts as a spring element, as stated above. During screw insertion, the collar 34 internal diameter collapses around the body portion 32. This reduces the major diameter effectively caused by the collar 34. The projection 42 allows the screw shank portion 14" to turn the collar 34, as if the collar 34 and shank portion 14" were one component. If bone resorbtion occurs or bone damage, the collar 34 can grow outwardly to the expanded condition to compensate for this problem.

While the embodiment shown in FIGS. 8-11 include the single projection 42 and slot formed between edges 38 and 40, the collar 34 can be split with more than one slot and even tapered to provide more force and/or interference towards the tip which may be beneficial for better fixation in a cortical/cancellous bone structure, such as a pedicle. For this approach, the screw tapered end is compressed by a removable collar or instrument until insertion into the bone is started, or held by a lip of the screw 10 until insertion is complete.

Similar to prior art screw assemblies, the bone screw 10 of the present invention can include a coating over the thread. Preferred coatings can be selected from the group including bio-active, osteo-conductive, and osteo-inductive coatings. Likewise, a portion of the shank portion 14, 14', 14", and thread 16, 16', 16" can be textured by means well known in the art. Additionally, specific coatings can be used as are well known in the art, including titanium, nitride, titanium oxides, diamond-like coatings, and other surface modifying agents. The screw member 10 itself can be made from various materials known in the art, including titanium, titanium alloys, stainless steels, cobalt chrome, and bio-resorbable materials, such as those discussed above.

In use, most generally, the present invention provides a method of inserting a bone screw 10 in to a bone by threading the screw 10, 10', 10" into a bone and forming a complementary threaded socket with the bone. The thread 16, 16', 16" expands from the screw into the threaded socket as the threaded socket expands with wear over time. The bone screw is maintained in the socket formed by the screw 10 in a bone by expanding the thread 16, 16', 16" of the screw 10, 10', 10" into complementary threads of the socket as the socket wears away over time. As discussed above, the socket can be formed by the bone screw 10 or the socket can be first be formed and then the bone screw inserted into the socket while maintaining the expandable thread portion 16, 16', 16" of the screw shank portion 14, 14', 14" in the compressed condition. More specifically, the socket will include a helical recess therein which is either cut by the drive element 28, 28', 28" into the socket alone or in combination with the threaded portion 16, 16', 16". In either event, as the helical recesses of the socket expand during wear over time, or with remodeling, the threaded portion 16 expands into the helical recess. Accordingly, the drive element 28, 28', 28" either cuts the helical recess in the socket alone, or with the threaded portion 16, 16', 16".

The unique approach of the present invention allows distinct advantages over prior art. First, such an approach allows for better fit and fill of the socket in which the thread is inserted, especially when the interface changes from cortical to cancellous bone. For the self tapping version shown in FIGS. 5-7, when the screw 10 is initially inserted into the bone, the screw 10 cuts a relatively perfect matching thread into the bone wall. The active thread section 16, 16', 16" is compressed into the minimum diameter during insertion and engages this matching thread of the bone.

Obviously many modifications and variations of the present invention are possible in light of the above teachings. It is, therefore, to be understood that within the scope of the appended claims the invention may be practiced otherwise than as specifically described.

What is claimed:

1. A bone screw comprising:
   a head portion and
   a shank portion, said shank portion including a longitudinally extending helical thread including an edge, the edge including a helical groove extending along a longitudinal axis of the shank portion and a helical spring member disposed within at least a portion of the groove, the spring member flexing inwardly and outwardly from said longitudinal axis relative to said shank portion.

2. The bone screw set forth in claim 1, wherein said spring member has a compressed condition wherein said shank portion is adapted to be seated within a socket which compresses said spring member radially inwardly into said groove and an expanded condition wherein said spring member is adapted to expand radially outwardly into a groove formed into the socket, complementary to said spring member, as the groove wears over time.

3. The bone screw as set forth in claim 1, wherein said groove includes a linear length greater than a length of said spring member when said spring member is in said expanded condition allowing for linear growth of said spring member as said spring member is compressed into said compressed condition.

4. The bone screw as set forth in claim 1, wherein said spring member includes a rectangular cross sectional shape.

5. The bone screw as set forth in claim 1, wherein said spring member includes a round cross sectional shape.

6. The bone screw as set forth in claim 1, wherein said spring member includes an oval cross sectional shape.

7. The bone screw as set forth in claim 1, wherein at least a portion of said shank portion and thread taper radially inwardly from said head portion toward an opposite edge of said shank portion.

8. The bone screw as set forth in claim 1, including a coating over said thread selected from a group consisting of bioactive, osteo-conductive, and osteo-inductive coatings.

9. The bone screw as set forth in claim 1, wherein at least a portion of said shank portion and thread are textured.

10. The bone screw as set forth in claim 1, including a coating selected from the group consisting of titanium nitrite, titanium oxides, diamond-like coatings, and surface modifying agents.

11. The bone screw as set forth in claim 1, made from a material selected from a group consisting of titanium, titanium alloys, stainless steels, cobalt chrome, and bioresorbable materials.

* * * * *